United States Patent

Tobiki et al.

[11] 3,992,371
[45] Nov. 16, 1976

[54] PENICILLINS SUBSTITUTED WITH HETEROCYCLIC AND SUBSTITUTED PHENYL GROUPS

[75] Inventors: Hisao Tobiki, Kobe; Hirotada Yamada; Iwao Nakatsuka, both of Nishinomiya; Kozo Shimago, Takarazuka; Shigeru Okano, Kawanishi; Takenari Nakagome, Nishinomiya; Toshiaki Komatsu, Takarazuka; Akio Izawa, Kawanishi; Hiroshi Noguchi, Nishinomiya; Yasuko Eda, Toyonaka, all of Japan

[73] Assignee: Sumitomo Chemical Company, Limited, Japan

[22] Filed: Dec. 24, 1974

[21] Appl. No.: 536,181

[30] Foreign Application Priority Data
Dec. 27, 1973 Japan................................ 49-1799

[52] U.S. Cl............................ 260/239.1; 424/250; 424/251; 424/256; 424/258
[51] Int. Cl.$^2$........................................ C07D 499/70
[58] Field of Search.............................. 260/239.1

[56] References Cited
UNITED STATES PATENTS

| | | | |
|---|---|---|---|
| 2,985,648 | 5/1961 | Doyle et al. ................. | 260/239.1 |
| 3,268,513 | 8/1966 | Grant et al. .................. | 260/239.1 |
| 3,381,001 | 4/1968 | McGregor ..................... | 260/239.1 |
| 3,454,557 | 7/1969 | Putchett et al. ............. | 260/239.1 |
| 3,579,501 | 5/1971 | McGregor ..................... | 260/239.1 |
| 3,864,329 | 2/1975 | Tobihe et al. ................ | 260/239.1 |

*Primary Examiner*—Gerald A. Schwartz
*Attorney, Agent, or Firm*—Stewart and Kolasch, Ltd.

[57] ABSTRACT

Novel penicillins of the formula

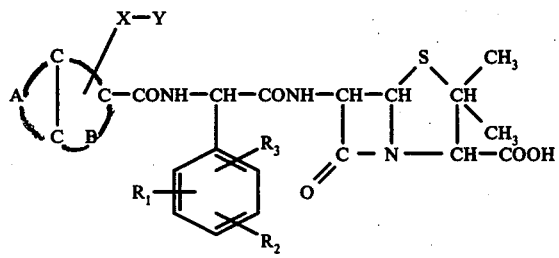

wherein

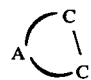

represents a substituted or unsubstituted benzene or nitrogen atom-containing heteroaromatic ring which may be substituted,

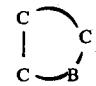

represents a pyridine, pyrazine or pyridazine ring, X represents an oxygen or sulfur atom, Y represents a hydrogen atom or a lower alkoxycarbonyl or lower alkanoyl group, and $R_1$, $R_2$ and $R_3$ are each a hydrogen or halogen atom or a nitro, lower alkylamino, di(-lower)alkylamino, amino, lower alkoxycarbonylamino, lower alkanoylamino, amino(lower)alkyl, lower alkyl, lower alkoxy, hydroxyl, sulfamoyl, trifluoromethyl, lower alkylthio or lower alkylsulfonyl group, excluding the cases where all of $R_1$, $R_2$ and $R_3$ are hydrogen atoms and where $R_1$ is a hydroxyl group and $R_2$ and $R_3$ are each a hydrogen or halogen atom, and their non-toxic, pharmaceutically acceptable salts, which can be prepared by reacting a carboxylic acid of the formula:

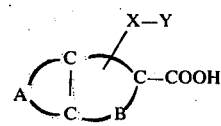

wherein

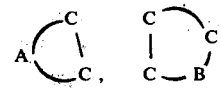

X and Y are each as defined above or its reactive derivative with a compound of the formula:

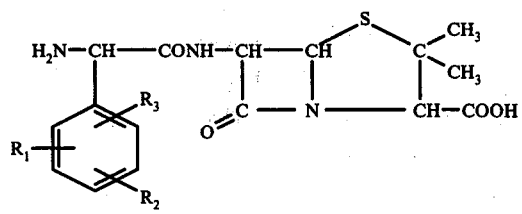

wherein $R_1$, $R_2$ and $R_3$ are each as defined above or its reactive derivative, and are useful as antimicrobial agents against gram-positive and gram-negative bacteria including Pseudomonas.

25 Claims, No Drawings

PENICILLINS SUBSTITUTED WITH HETEROCYCLIC AND SUBSTITUTED PHENYL GROUPS

The present invention relates to novel penicillins and their preparation. More particularly, it relates to novel penicillins and their non-toxic, pharmaceutically acceptable salts, which are useful as antimicrobial agents having a broad antimicrobial spectrum including Pseudomonas, and to their preparation.

It is well known that 6-(α-aminoacylamido)penicillanic acid derivatives such as 6-(α-aminophenylacetamido)penicillanic acid (Ampicillin), 6-(α-amino-p-hydroxyphenylacetamido)penicillanic acid (Amoxycillin),6(α-amino-thienylacetamido)penicillanic acid, 6-(1-amino-cyclohexanecarboxamide)-penicillanic acid (Cyclacillin), 6-(α-amino-isothiazolylacetamido)penicillanic acid and 6-[α-amino-2-1,4-hexadienylacetamido)]penicillanic acid (Epicillin) inhibit the growth of various gram-positive and gram-negative bacteria. Particularly, ampicillin is one of the excellent chemotherapeutics. These compounds, however, do not exert any appreciable antimicrobial activity against Pseudomonas. In U.S. Pat. No. 3,433,784, there are described some N-acyl derivatives of ampicillin which show a minimal inhibitory concentration of 125 to 250 μg/ml against Pseudomonas pyocinea A or R 59, when determined by the standard test method. The anti-Pseudomonas activity of the compounds as described in the working examples is, however, not so high and the antimicrobial activity against other gram-positive and gram-negative bacteria is considerably low. Thus, it may be said that the N-acyl derivatives of ampicillin are less valuable than ampicillin itself from the practical viewpoint.

As the result of the study seeking novel penicillins which have a broad antimicrobial spectrum and are highly active against gram-positive and gram-negative bacteria including Pseudomonas, it has been found that, among various compounds, the penicillins of the following formula characteristically exhibit a noticeable antimicrobial activity against Pseudomonas and a broad antimicrobial spectrum:

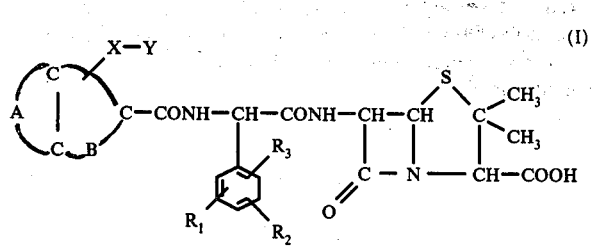

wherein

is a benzene ring or a 5- or 6-membered heteroaromatic ring containing a nitrogen atom as the hetero atom, which may have one or more substituents selected from the group consisting of lower alkyl, lower alkoxy, lower alkylthio, lower alkylsulfonyl, halo(lower)alkyl, halogen, hydroxyl, nitro, free or protected amino, lower alkylamino, di(lower)alkylamino, lower alkanoylamino, pyrrolidino and morpholino, and may form a bicyclic ring together with a cyclo(lower)alkyl ring, a lower alkylenedioxy ring, a lower alkyleneoxy ring or a thiazole ring, is a pyridine, a pyrazine ring or a pyridazine ring, X is an oxygen atom or a sulfur atom, Y is a hydrogen atom, a lower alkoxycarbonyl group or a lower alkanoyl group and $R_1$, $R_2$ and $R_3$ are each a hydrogen atom, a halogen atom, a nitro group, a lower alkylamino group, a di(lower)alkylamino group, an amino group, a lower alkoxycarbonylamino group, a lower alkanoylamino group, an amino(lower)alkyl group, a lower alkyl group, a lower alkoxy group, a hydroxyl group, a sulfamoyl group, a trifluoromethyl group, a lower alkylthio group or a lower alkylsulfonyl group, excluding the cases where all of $R_1$, $R_2$ and $R_3$ are hydrogen atoms and where $R_1$ is a hydroxyl group and $R_2$ and $R_3$ are each a hydrogen atom or a halogen atom.

Accordingly, a main object of the present invention is to provide novel penicillins (I) and their non-toxic salts, which are useful as antimicrobial agents. Another object of this invention is to provide a process for preparing the penicillins (I) and their non-toxic salts. A further object of the invention is to provide a use of the penicillins (I) and their non-toxic salts as antimicrobial agents. These and other objects of the invention will be apparent to those conversant with the art from the foregoing and subsequent descriptions.

As to the significances of the symbols in the said formula (I) and in any other formula as hereinafter shown, the term "lower alkyl" is intended to mean generally both straight and branched chain aliphatic hydrocarbon groups having not more than eight carbon atoms (preferably not more than five carbon atoms) such as methyl, ethyl, propyl, isopropyl, butyl, isobutyl, amyl and isoamyl. Similarly where the term "lower" is used as a part of the description of any other group (e.g. lower alkoxy, alkylthio, halo(lower)alkyl, lower alkylamino, di(lower)alkylamino), it is referred to the alkyl portion of such group. Thus, the terms "lower alkanoyl" and "lower alkoxycarbonyl" mean respectively alkanoyl and alkoxycarbonyl having not more than nine carbon atoms (preferably not more than six carbon atoms). Exceptionally, however, the term "lower alkylenedioxy" indicates alkylenedioxy having not more than three carbon atoms. The halogen atom includes chlorine atom, bromine atom, iodine atom and fluorine atom.

The protected amino group indicates an amino group which is protected by any protective group conventionally employed for the protection of amino. Examples of the protected amino group include o-nitrophenylsulfenylamino, acetoacetylamino and benzyloxycarbonylamino.

The 5- or 6-membered heteroaromatic ring containing one or two nitrogen atoms may be, for example, a pyrazole ring, a thiazole ring, a pyridine ring, a pyrazine ring, a pyridazine ring, a pyrimidine ring, etc. Among them, preferred are a pyrazole ring, a thiazole ring, a pyrazine ring and a pyrimidine ring, particularly a pyridine ring.

The non-toxic, pharmaceutically acceptable salts of the penicillins (I) are, for instance, the alkali metal salts (e.g. sodium, potassium salts), the alkaline earth metal salts (e.g. calcium, magnesium salts), the arginine salt, the substituted and unsubstituted ammonium salts, etc. Examples of the substituted ammonium salts include the salts of triethylamine, procaine, dibenzylamine, N-benzyl-β-phenethylamine, 1-ephenamine, N,N'-dibenzylethylenediamine, dehydroabiethylamine, N,N'-bis-dehydroabiethylethylenediamine, etc.

One of the structural characteristics of the penicillins (I) of the invention is that the residue

bears thereon the substituent —X-Y linked to a carbon atom adjacent to the carbon atom to which a 6-(α-carbamoylacylamido)penicillanic acid moiety is linked. The compounds wherein the residue

bears no such substituent are antimicrobially much less active than those bearing the substituent and exhibit only the same low antimicrobial activity as those disclosed in U.S. Pat. No. 3,433,784 against Pseudomonas as well as other gram-positive and gram-negative bacteria.

Another structural characteristic of the penicillins (I) is the presence of the substituents ($R_1$, $R_2$ and $R_3$) on the phenyl group as defined above. The serum and urinary concentrations in mice and rats of the compounds wherein the phenyl group bears the substituents $R_1$, $R_2$ and $R_3$ are higher than those of the compounds not having such substituents. The excellent antibacterial activity and the high serum and urinary concentrations of the penicillins (I) wherein at least one of the substituents ($R_1$, $R_2$ and $R_3$) is amino, amino(lower)alkyl, lower alkylamino or di(lower)alkylamino, lower alkanoylamino, hydroxyl or lower alkoxy are particularly notable.

Among the penicillins (I), one preferred class is the compounds of the following formula (I-A):

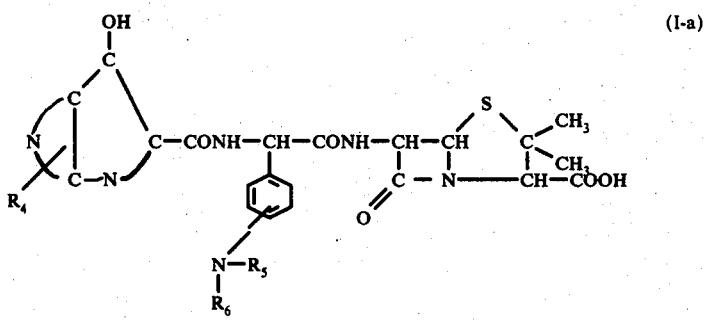

wherein

and

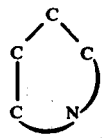

each mean a pyridine ring, $R_4$ means a hydrogen atom, a halogen atom, a lower alkyl group, a lower alkoxy group, a lower alkylthio group, a hydroxyl group, a di(lower)alkylamino group or a lower alkanoylamino group and $R_5$ and $R_6$ are each a hydrogen atom, a lower alkyl group or a lower alkanoyl group, and their non-toxic pharmaceutically acceptable salts. Particularly the compound (I-a) wherein $R_4$ is hydrogen, methyl, methoxy or acetamido, $R_5$ is hydrogen, $R_6$ is hydrogen or acetyl and

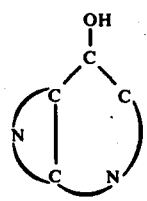

represents a 4-hydroxy-1,5-naphthyridine ring shows excellent antibiotic properties.

Another preferred class of the penicillins (I) is the compounds of the formula (I-B):

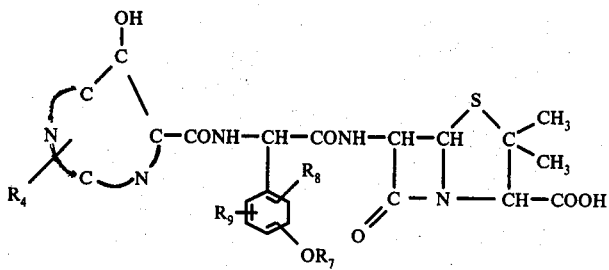

wherein

and

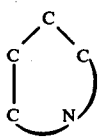

are each a pyridine ring, $R_4$ is as defined above, $R_7$ is a hydrogen atom or a lower alkyl group, $R_8$ is a lower alkyl group, an amino group, a lower alkanoylamino group, a lower alkoxy group or a hydroxyl group and $R_9$ is a hydrogen atom, a lower alkyl group, a lower alkoxy group or a hydroxyl group. Particularly preferred compounds (I-b) are those wherein

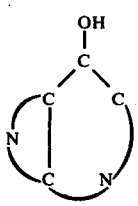

represents a 4-hydroxy-1,5-naphthyridine ring, $R_4$ is hydrogen, methyl, methoxy or acetamido, $R_7$ is hydrogen or methyl, $R_8$ is methyl, amino, acetamido, methoxy or hydroxyl and $R_9$ is hydrogen, methyl, methoxy or hydroxyl.

The presence of the substituents defined above as

—$OR_7$, $R_8$ or $R_9$ on the phenyl group makes the antibiotic activity of the resulting compounds excellent.

According to the present invention, the penicillin (I) can be produced by reacting a compound of the formula (II):

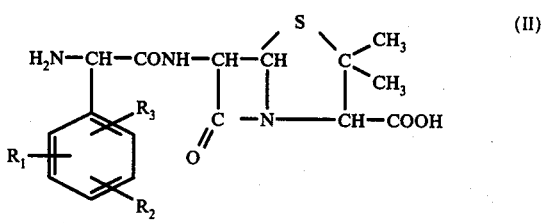

(II)

wherein $R_1$, $R_2$ and $R_3$ are each as defined above, or its derivative with a compound of the formula (III):

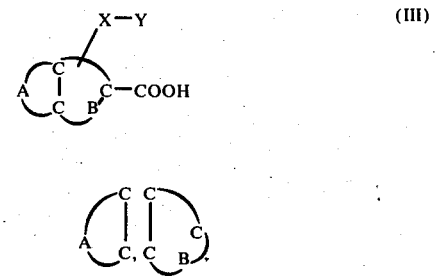

(III)

wherein

X and Y are each as defined above, or its reactive derivative, if necessary, followed by elimination of any protective group.

The reaction between the compound (II) or its derivative and the compound (III) or its reactive derivative is usually carried out in an inert solvent such as a polar solvent (e.g. dichloromethane, chloroform, acetone, tetrahydrofuran, dioxane, acetonitrile, methylisobutylketone, ethanol, dimethylformamide), a non-polar solvent (e.g. benzene, toluene, petroleum ether, n-hexane) or their mixture. In some cases, there may be used an aqueous medium. The reaction temperature is not limitative and may be usually below 50° C, preferably from —80° to 50° C.

The derivative of the compound (II) may be, for example, salts, esters, and N-substituted compounds thereof. Examples of the salts are salts of alkali metals (e.g. sodium, potassium), alkaline earth metals (e.g. calcium, barium), organic bases (e.g. trimethylamine, triethylamine) and organic sulfonic acids (e.g. toluenesulfonic acid, naphthalenesulfonic acid, tetrahydronaphthalenesulfonic acid). Examples of the esters and the N-substituted compounds are as follows:

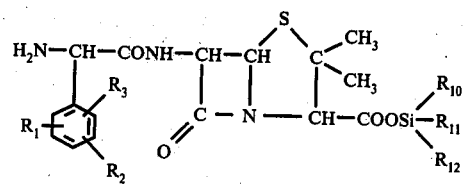

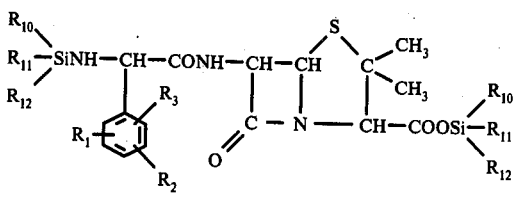

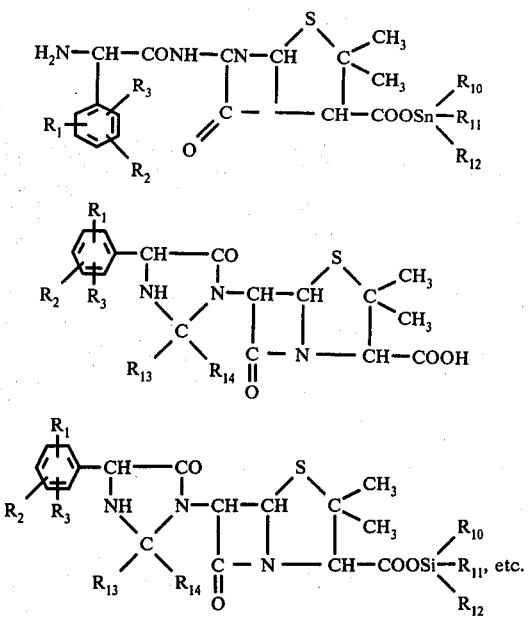

wherein $R_{10}$, $R_{11}$, $R_{12}$, $R_{13}$ and $R_{14}$ are each a lower alkyl group and $R_1$, $R_2$ and $R_3$ are each as defined above.

These esters can be advantageously used in the coupling reaction, because of their higher solubility in an ordinary solvent to be used as the reaction medium and of their higher reactivity with the compound (II) than those of the corresponding free acids.

Further examples of the ester unit in the esters of the compound (II) are as follows: toluenesulfonylethyl ester, p-nitrobenzyl ester, benzyl ester, phenacyl ester, diphenylmethyl ester, substituted diphenylmethyl ester, trityl ester, benzoyloxymethyl ester, lower alkanoyloxymethyl ester, dimethylmethyleneamino ester, p-nitrophenyl ester, methylsulfonylphenyl ester, methylthiophenyl ester, t-butyl ester, 3,5-di-t-butyl-4-hydroxybenzyl ester, trichloroethyl ester, etc. These ester units are all conventionally employed as a group protecting a carboxylic acid radical in the related art field.

The esters which can be prepared commercially from penicillin-G are particularly preferable. Examples of the preparation for such esters are illustratively shown in the following scheme:

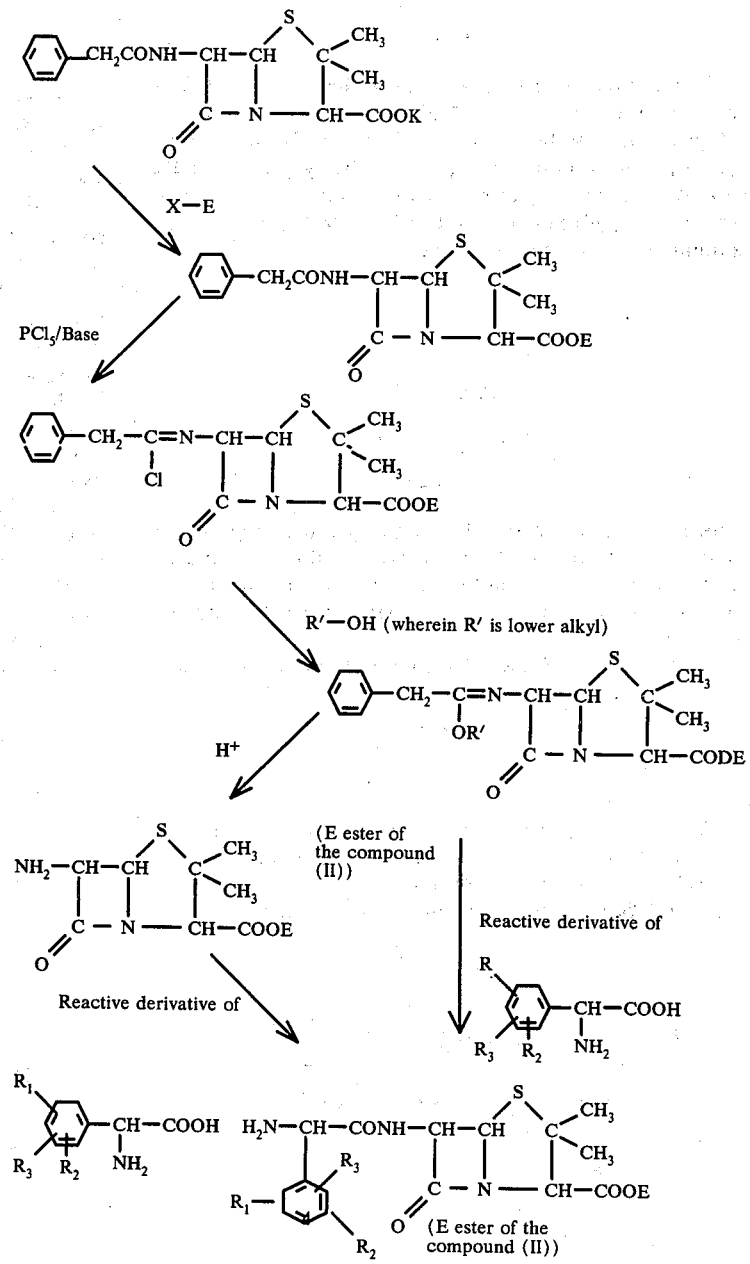

wherein $R_1$, $R_2$ and $R_3$ are each as defined above, and -COOE means an ester moiety.

The above illustrated E ester of the compound (II) can be employed for the coupling reaction in the form of a salt with an organic or inorganic acid. Examples of the organic or inorganic acid moiety in such salt are toluenesulfonic acid, naphthalenesulfonic acid, tetralinesulfonic acid, hydrochloric acid, etc.

After the coupling reaction with the compound (III) or its reactive derivative, these ester moieties can be eliminated using a per se conventional procedure such as catalytic reduction or hydrolysis under mild conditions so as not to affect the β-lactam ring of the penicillin nucleus.

The compound (III) may be used as such, i.e. in a free or salt form, or as the reactive derivative.

Examples of the salts of the compound (III) are the salts of alkali metals, alkaline earth metals, ammonia and organic bases (e.g. trimethylamine, triethylamine, dicyclohexylamine).

The reactive derivatives of the compound (III) on the carboxyl group include, for instance, acid halides, acid anhydrides, azolides, acid azides and active esters.

Among the acid halides, the use of an acid chloride is the most favorable. Examples of the acid anhydrides are mixed acid anhydrides and symmetric acid anhydrides prepared by the use of acids such as toluenesulfonic acid, an alkylcarbonic acid and an aliphatic carboxylic acid (e.g. pivalic acid). Examples of the azolides are those obtained by using imidazole, dimethylpyrazole, triazole, tetrazole or the like. Examples of the active esters are those prepared by using p-nitrophenol, pentachlorophenol, p-nitrothiophenol, N,N'-dimethylhydroxylamine, 1-hydroxy-2(1H)-pyridone, N-hydroxysuccinimide or N-hydroxyphthalimide.

When the compound (III) wherein Y is hydrogen or its reactive derivative is used, the hydroxyl group and the mercapto group may be protected with any protective group as conventionally employed in the related art field.

Illustrating some of the reactive derivatives of the compound (III) in details, the mixed acid anhydride of the formula:

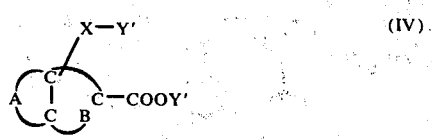

(IV)

wherein

and X are as defined above and Y' is acyl or alkoxycarbonyl can be prepared by reaction of the compound (III) wherein Y is hydrogen with an acyl halide or an alkyl halocarbonate. Thus, the reaction of 1 molar amount of the compound (III) with 2 molar amounts of an acyl halide (e.g. pivaloyl chloride) or an alkyl halocarbonate (e.g. ethyl chlorocarbonate, isobutyl chlorocarbonate) in the presence of 2 molar amounts of a basic substance may afford the compound (IV) in an excellent yield.

Another type of the reactive derivative is the compound of the formula:

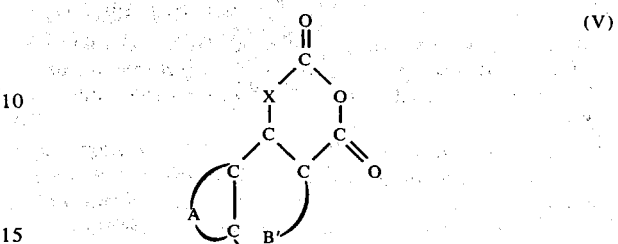

wherein

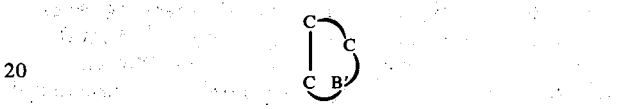

is the same meaning as defined with respect to

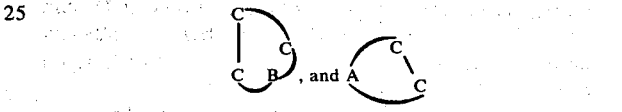

and X are each as defined above, which may be prepared by the reaction of 1 molar amount of the compound (III) with 1 molar amount of phosgene in the presence of 2 molar amounts of a basic substance.

Examples of the basic substance in the said reactions are an inorganic base (e.g. sodium hydroxide, potassium hydroxide) and an organic base (e.g. triethylamine, pyridine, dimethylaniline, lutidine, N-methylmorpholine, N-methylpiperidine).

The thus prepared reactive derivatives can be used in the form of the reaction mixture in the reaction with the compound (II).

When the compound (III) is employed in the form of a free acid or a salt, there is preferably used a coupling reagent such as N,N'-dicyclohexylcarbodiimide, N-cyclohexyl-N'-morpholinoethylcarbodiimide, triphenylphosphine or 2-ethyl-5-(m-sulfonyl)-isoxazolium hydroxide inner salt in the reaction with the compound (II). In case of using such coupling reagent, the reaction often proceeds through the activated state of the carboxyl group in the compound (III), or the activated state of the amino group in the compound (II).

In the compound (III), the substituent —X—Y may represent either a free hydroxyl or sulfhydryl group or a protected hydroxyl or sulfhydryl group. When the compound (III) wherein the substituent —X—Y represents a protected hydroxyl or sulfhydryl group is employed in the coupling reaction, the penicillin (I) wherein Y is hydrogen may be often obtained as the result of simultaneous elimination of the protective group. When the protective group is not eliminated in the course of coupling reaction, it may be eliminated thereafter by a conventional procedure under such a mild condition that the opening of the lactam ring in the penicillin nucleus is not caused. The elimination of the protective group can be accomplished, for instance, by treating the product in the coupling reaction with an inorganic or organic basic substance (e.g. sodium carbonate, potassium carbonate, sodium hydroxide, aqueous ammonia solution, triethylamine, methylamine, dimethylamine, diethylamine, morpholine, piperidine, potassium acetate, sodium acetate, potassium 2-ethylhexanoate). In such treatment, the penicillin (I) wherein Y is hydrogen can be obtained even in an acidic condition, but the protective group is more smoothly eliminated by treatment under a basic condition.

When the compound (III) wherein Y is hydrogen is subjected to coupling, it may be favorably employed, for instance, in the form of the reactive ester or the acid halide on the carboxyl group whereby the penicillin (I) wherein Y is hydrogen is obtainable as the product.

On production of the penicillin (I) of which at least one of $R_1$, $R_2$ or $R_3$ on the phenyl group is amino, lower alkylamino or amino(lower)alkyl, (lower) alkyl, the coupling reaction may be carried out while protecting the amino moiety in such group with a conventional protective group commonly used in the related art field such as penicillins, cephalosporins or peptides, but the said protection is not always necessary because the amino group at the α-position of the compound (II) can be predominantly acylated due to its higher reactivity than that of the amino moiety substituted on the phenyl group.

It can also be produced from the corresponding penicillin (I) having a substituent commonly used for formation of the amino moiety (e.g. cyano, nitro, nitroso, oxime, Schiff's base, azide, etc.) by reducing the substituent to amino, lower alkylamino or amino(lower)alkyl. (lower) alkyl. The penicillin (I) to be used as the starting material may be produced by the same procedure as illustrated above.

The penicillin (I) wherein

is substituted with an amino group may be produced from the corresponding penicillin (I) wherein

is substituted with a nitro group or a protected amino group. For example, the reduction of the penicillin (I) wherein

bears a nitro group or a benzyloxycarbonylamino group under such a mild condition that the opening of the lactam ring in penicillin nucleus is not caused gives the penicillin (I) wherein

bears an amino group. Further, for example, the hydrolysis of the penicillin (I) wherein

bears a protected amino group (e.g. enamine) under a mild condition as above results in the elimination of the protective group to give the penicillin (I) wherein

bears an amino group.

Alternatively, the penicillin (I) having an amino group on

may be produced by the said coupling reaction wherein the compound (II) is used in the form of the acid halide on the carboxyl group.

When any protective group is present in the product of the coupling reaction, it may be eliminated by a per se conventional procedure such as catalytic reduction or hydrolysis, favorably under a mild condition.

The penicillin of the formula (I):

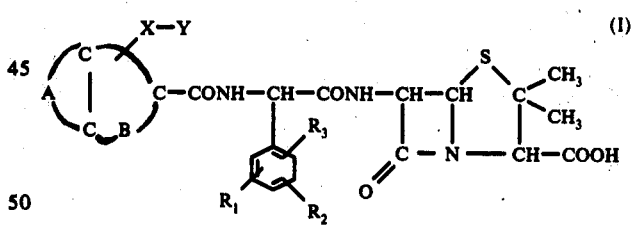

wherein

X, Y, $R_1$, $R_2$ and $R_3$ are each as defined above can also be prepared by reacting a compound (VI):

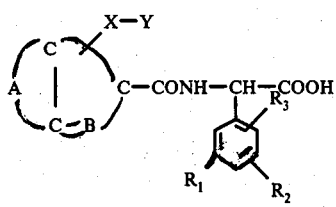

wherein

X, Y, $R_1$, $R_2$ and $R_3$ are each as defined above or its reactive derivative with a compound of the formula (VII):

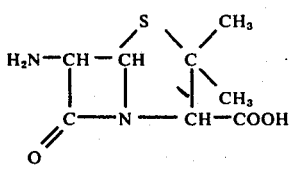

or its reactive derivative in the substantially same manner as mentioned above.

Still, the compound (VI) can be prepared easily in a conventional procedure, for instance, by reacting the reactive derivative of the compound (III) with an amino acid of the formula (VIII):

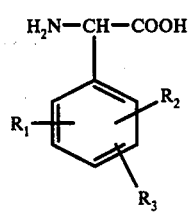

wherein $R_1$, $R_2$ and $R_3$ are each as defined above, or its ester in water or an organic solvent in the presence of a basic substance.

The amino acid may be any of the DL-, D- and L-configurations. The ester may be, for example, the trialkylsilyl ester, lower alkyl ester, p-nitrophenyl ester, benzyl ester, phenylthiophenyl ester, N-hydroxysuccinimide ester, etc. These esters may be derived from the corresponding acid chlorides or prepared by any other conventional method. As the organic solvent, a polar or non-polar organic solvent (e.g. dioxane, tetrahydrofuran, dichloromethane, benzene, dimethylformamide, dimethylsulfoxide) is utilizable. Examples of the basic substance are sodium hydroxide, potassium hydroxide, triethylamine, N-methylmorpholine, dimethylaniline, etc.

When the ester is employed in the above reaction, the protective group of the resulting N-acylamino acid ester may be eliminated by a conventional procedure to give the compound (VI). When desired, the obtained active ester salt of the compound (VI) may be employed in the coupling reaction with the compound (VII) to produce the penicillin (I).

The produced penicillin (I) may be, if desired, converted into its non-toxic pharmaceutically acceptable salt in a per se conventional manner.

The production of the penicillin (I) may be identified by thin layer chromatography, iodometry, infrared absorption spectrum and so on. The characteristical infrared absorption due to the lactam ring is at 1750 – 1800 cm$^{-1}$. A particularly effective identifying method is NMR analysis, since the signals attributed to the proton Ha of the amide bond in the following structure for the penicillin (I) appear in a very low-field, which is due to the presence of the substituent —X—Y:

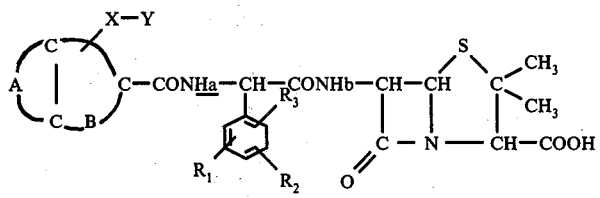

When measured in hexadeuterodimethylsulfoxide at 60 MHz using an NMR-spectral instrument, Ha and Hb signals in case of Y being a lower alkanoyl group or a lower alkoxycarbonyl group appear respectively at 540 – 570 Hz and at 630 – 680 Hz. In case of Y being a hydrogen atom, Ha and Hb signals appear respectively at 650 – 690 Hz and at 540 – 570 Hz. Ha and Hb signals in case of Y being a hydrogen atom appear in a lower field than those of Y being a lower alkanoyl group or a lower alkoxycarbonyl group.

The following examples are given to illustrate the invention more precisely, but not in any way to limit the invention.

EXAMPLE 1

Preparation of D-α-(4-hydroxy-1,5-naphthyridine-3-carboxamido)-m-aminobenzylpenicillin sodium salt:-

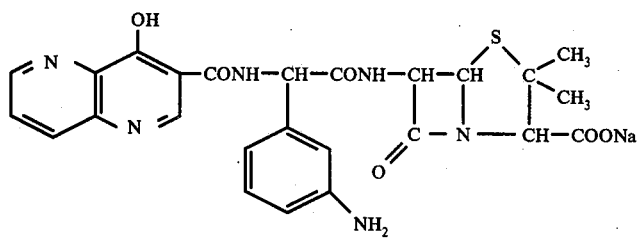

a. Preparation of 4-hydroxy-1,5-naphthyridine-3-carboxylic acid N-hydroxysuccinimide ester.

To a mixture of 7.6 g. of 4-hydroxy-1,5-naphthyridine-3-carboxylic acid, 5.06 g of N-hydroxysuccinimide and 150 ml of dimethylformamide, 5.72 g of thionyl chloride were added dropwise at a temperature below 10° C, and the resulting mixture was stirred at room temperature for 16 hours. To the reaction mixture, there were added dropwise 8.23 g of pyridine at a temperature below 10° C, and stirring was carried out for 4 hours at room temperature. The precipitated crystals were collected by filtration, washed with dimethylformamide and acetone in order and dried to give 11.2 g of the objective compound, M.P. 294 – 295° C (decomposition).

b. Preparation of D-α-(4-hydroxy-1,5-naphthyridine-3-carboxamido)-m-aminobenzylpenicillin triethylamine salt.

To a solution of 4.63 g of D-α-amino-m-aminobenzylpenicillin triethylamine salt in 14 ml of dimethylformamide, 2.58 g of 4-hydroxy-1,5-naphthyridine-3-carboxylic acid N-hydroxysuccinimide ester and 0.9 g of triethylamine were added, and stirring was carried out at room temperature for 1 hour. After removal of insoluble materials from the reaction mixture, 100 ml of dichloromethane were added thereto and cooled with ice for 1 hour. The precipitated crystals were collected by filtration, washed with dichloromethane and dried under reduced pressure to give 4.9 g of the objective compound. Purity (determined by iodometry), 92 %.

c. Preparation of D-α-(4-hydroxy-1,5-naphthyridine-3-carboxamido)-m-aminobenzylpenicillin sodium salt.

To 150 ml of dimethylformamide, there were added 3.3 g of D-α-(4-hydroxy-1,5-naphthyridine-3-carboxamido)-m-aminobenzylpenicillin triethylamine salt as obtained above and 0.93 g of sodium-2-ethylhexanoate, and then insoluble materials were removed by filtration. The dimethylformamide layer was added dropwise to 75 ml of acetone with stirring. The precipitated crystals were collected by filtration, washed with acetone and dried under reduced pressure to give 2.7 g of the objective compound. Purity (determined by iodometry), 90.5%.

carboxylic acid N-hydroxysuccinimide ester and 1.0 g of triethylamine were added and stirring was carried out at room temperature for 1.5 hours. After removal of insoluble materials from the reaction mixture by filtration, 100 ml of dichloroethane were added thereto and stirred for 2 hours. The precipitated crystals were collected by filtration, washed with dichloroethane and dried under reduced pressure to give D-α-(4-hydroxy-1,5-naphthyridine-3-carboxamido)-p-aminobenzylpenicillin triethylamine salt. To a mixture of 4.0 g of the triethylamine salt and 12 ml of dimethylformamide, 1.1 g of sodium-2-ethylhexanoate were added with stirring. The resulting mixture was added dropwise to 60 ml of acetone while stirring. The precipitated crystals were collected by filtration, washed with acetone and dried under reduced pressure to give the objective compound. Purity (determined by iodometry), 90.0 %.

b. A mixture of 4.8 g of D-α-amino-p-aminobenzylpenicillin phenacyl ester (prepared from 6-aminopenicillanic acid phenacyl ester and D-2-p-aminophenylglycine according to a conventional procedure), 45 ml of dimethylformamide, 2.7 g of 4-hydroxy-1,5-naphthyridine-3-carboxylic acid N-hydroxysuccinimide ester and 1.0 g of triethylamine was stirred at room temperature for 1 hour. The resulting mixture was poured into 1 % aqueous solution of sodium bicarbonate. The precipitated crystals were collected by filtration, washed with water and acetone in order and dried under reduced pressure to give 4.7 g of D-α-(4-hydroxy-1,5-naphthyridine-3-carboxamido)-p-aminobenzylpenicillin phenacyl ester.

To a mixture of 4.7 g of the phenacyl ester and 80 ml of dimethylformamide, 2.24 g of sodium thiophenolate were added, and stirring was carried out for 1 hour. The resulting mixture was poured into 320 ml of acetone. The precipitated crystals were collected by filtration, washed with acetone and dried to give 3.76 g of the objective compound.

EXAMPLE 3

Preparation of D-α-(4-ethoxycarbonyloxy-1,5-naphthyridine-3-carboxamido)-p-methoxybenzylpenicillin:-

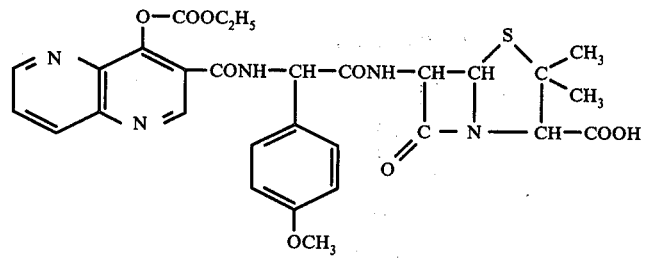

EXAMPLE 2

Preparation of D-α-(4-hydroxy-1,5-naphthyridine-3-carboxamido)-p-aminobenzylpenicillin sodium salt:-

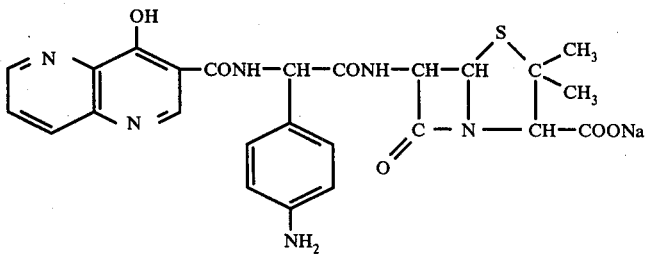

a. To a solution of 4.63 g of D-α-amino-p-aminobenzylpenicillin triethylamine salt in 14 ml of dimethylformamide, 2.7 g of 4-hydroxy-1,5-naphthyridine-3-

To a mixture of 1.9 g of 4-hydroxy-1,5-naphthyridine-3-carboxylic acid, 50 ml of dichloromethane and 2.2 g of triethylamine, which was cooled at 0°– 5° C, 2.18 g of ethyl chlorocarbonate were added. The resulting mixture was allowed to stand for 30 minutes, 4.8 g of D-p-methoxybenzylpenicillin triethylamine salt were added thereto, and stirring was continued at 0°–5° C for 5 hours. The resulting mixture was adjusted to pH 1.5 with about 10 % dioxane solution of hydrogen chloride, and the solvent was distilled off under reduced pressure. The residue was added to 60 ml of ice water and stirred. Insoluble materials were collected by filtration, washed with water and dried under reduced pressure. Thus obtained crystals were powdered and added to 60 ml of ethylacetate. The mixture was stirred for 1 hour, and insoluble crystals were collected by filtration and dried to give 4.4 g of the objective compound. Purity (determined by iodometry), 85.5 %.

EXAMPLE 4

Preparation of D-α-(4-hydroxy-1,5-naphthyridine-3-carboxamido)-p-methoxybenzylpenicillin sodium salt:- a. To a solution of 0.7 g of D-α-amino-p-dimethylaminobenzylpenicillin β-naphthalene sulfonic acid salt in dimethylformamide, there were added 0.257 g of triethylamine and 10 g of molecular sieve R-3A, and stirring was continued for 1 hour. Then, the molecular sieve was removed by filtration. To the resulting mixture, 0.322 g of 4-hydroxy-1,5-naphthyridine-3-carboxylic acid N-hydroxysuccinimide ester and 0.257 g of triethylamine were added, the resultant mixture was stirred at room temperature for 5 hours. The reaction mixture was poured into 80 ml of acetone, and the precipitated crystals were collected by filtration to give 0.42 g of D-α-(4-hydroxy-1,5-naphthyridine-3-carboxamido)-p-dimethylaminobenzylpenicillin triethylamine salt. The thus obtained triethylamine salt was added to 5 ml of dimethylformamide and 0.128 g of sodium-2-

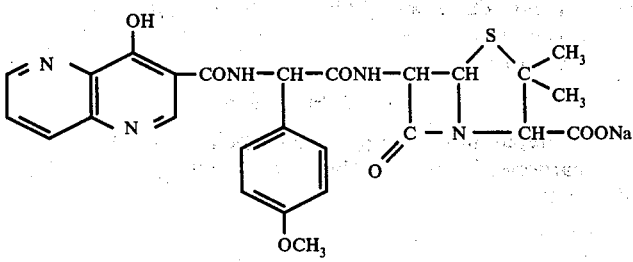

a. To a dried solution of 1.28 g of D-α-amino-p-methoxybenzylpenicillin in 12 ml of dimethylformamide and 1.31 g of triethylamine, 0.85 g of 4-hydroxy-1,5-naphthyridine-3-carboxylic acid N-hydroxysuccinimide ester was added, and stirring was continued. After the reaction was over, 200 ml of acetone were added thereto. The precipitated crystals were collected by filtration, washed with acetone and dichloromethane in order and dried to give 1.3 g of D-α-(4-hydroxy-1,5-naphthyridine-3-carboxamido)-p-methoxybenzylpenicillin triethylamine salt. The triethylamine salt was treated as in Example 1 (c) to give 0.05 g of the objective compound. Purity (determined by iodometry), 89 %.

b. To 1.25 g of D-α-(4-ethoxycarbonyloxy-1,5-naphthyridine-3-carboxamido)-p-methoxybenzylpenicillin, there were added 5 ml of dimethylformamide and 0.43 g of sodium 2-ethylhexanoate, and a small amount of insoluble materials was removed by filtration. The resulting mixture was added to 30 ml of acetone and stirred for 30 minutes. The precipitated crystals were collected by filtration, washed with acetone and dried to give 0.9 g of the objective compound. Purity (determined by iodometry), 85 %.

EXAMPLE 5

Preparation of D-α-(4-hydroxy-1,5-naphthyridine-3-carboxamido)-p-dimethylaminobenzylpenicillin sodium salt:- ethylhexanoate, and stirring was effected. The resulting mixture was poured into 30 ml of acetone, and the precipitated crystals were collected by filtration, washed with acetone and dried to give 0.32 g of the objective compound.

b. 4-Hydroxy-1,5-naphthyridine-3-carboxylic acid was added to a mixture of 0.73 g of dimethylformamide and 1.56 g of thionyl chloride in benzene with stirring, and stirring was continued at 40° – 85° C for 3 hours. The precipitated crystals were collected by filtration, washed with benzene and dried under reduced pressure to give 2.37 g of 4-hydroxy-1,5-naphthyridine-3-carbonyl chloride hydrochloride. Purity (determined by NMR analysis after esterification), 96.3 %.

To a mixture of 1.2 g of D-α-amino-p-dimethylaminobenzylpenicillin β-naphthalenesulfonic acid salt, 5 ml of dimethylformamide, 5 ml of dichloromethane and 0.81 g of triethylamine, 0.44 g of 4-hydroxy-1,5-naphthyridine-3-carbonylchloride hydrochloride was added, and stirring was continued for 3 hours. The reaction mixture was added to 50 ml of acetone. The precipitated crystals were collected by filtration and washed with acetone and dichloromethane in order to give 0.81 g of D-α-(4-hydroxy-1,5-naphthyridine-3-carboxamido)-p-dimethylaminobenzylpenicillin triethylamine salt.

The thus obtained triethylamine salt was converted into the corresponding sodium salt by treatment with sodium 2-ethylhexanoate in the same manner as above.

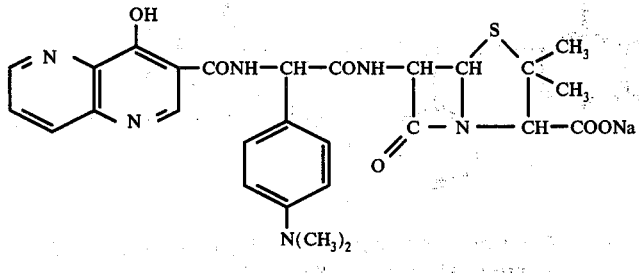

EXAMPLE 6

Preparation of D-α-(4-hydroxycinnoline-3-carboxamido)-m-aminobenzylpenicillin:-

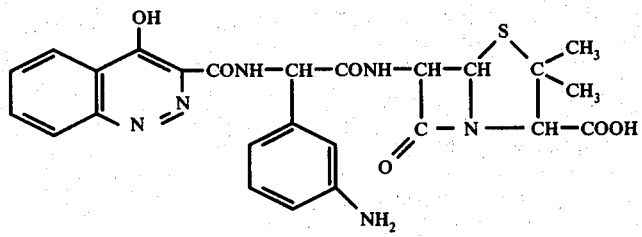

To a mixture of 0.95 g of 4-hydroxycinnoline-3-carboxylic acid and 30 ml of anhydrous dimethylformamide, there was added 0.89 g of N,N'-carbonyldiimidazole, and stirring was continued for 30 minutes. After the addition of 2.3 g of D-α-amino-m-aminobenzylpenicillin triethylamine salt, stirring was further continued for 3 hours. Then, 1.82 g of 50 % n-butanol solution of potassium 2-ethylhexanoate were added thereto, and the resultant mixture was added to acetone. The precipitated crystals were collected by filtration and dissolved in water. The solution was adjusted to pH 2 with N hydrochloric acid while cooling with ice. The precipitated product was separated and dried in vacuo over phosphorus pentoxide to give the objective compound. Purity (determined by iodometry), 89.5 %.

EXAMPLE 7

Preparation of D-α-(4-pivaloyloxyquinoline-3-carboxamido)-m-acetylaminobenzylpenicillin:-

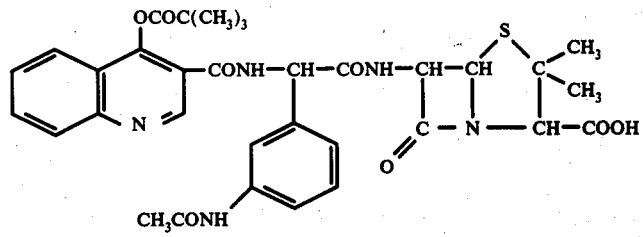

To a mixture of 1.88 g of 4-hydroxyquinoline-3-carboxylic acid, 50 ml of dichloroethane and 2.02 g of triethylamine, there were added dropwise 2.4 g of pivaloyl chloride at 0° – 5° C, and the resulting mixture was allowed to stand for 1 hour. After the addition of 5.1 g of D-α-amino-m-acetamidobenzylpenicillin triethylamine salt, the reaction was effected for 5 hours. The reaction mixture was added to a dilute aqueous solution of sodium bicarbonate, and unreacted materials were removed by shaking with ethyl acetate. The water layer was adjusted to pH 2 with dilute hydrochloric acid, and the precipitated crystals were extracted with ethyl acetate. The ethyl acetate layer was washed with water, dried over anhydrous magnesium sulfate and distilled under reduced pressure to eliminate the solvent. Ether was added to the residue to give the objective compound. Purity (determined by iodometry), 89 %.

EXAMPLE 8

Preparation of D-α-(4-hydroxy-1,5-naphthyridine-3-carboxamido)-m-nitrobenzylpenicillin triethylamine salt:-

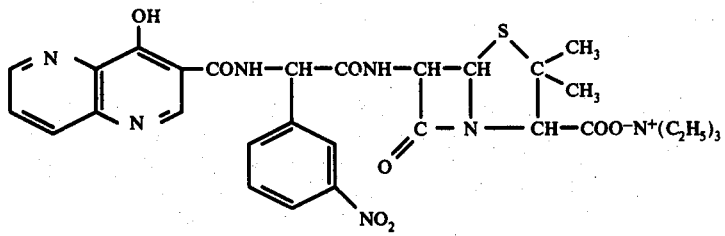

A mixture of 4.95 g of D-α-amino-m-nitrobenzylpenicillin triethylamine salt, 20 ml of dimethylformamide, 2.2 g of triethylamine and 2.87 g of 4-hydroxy-1,5-naphthyridine-3-carboxylic acid N-hydroxysuccinimide ester was stirred at room temperature for 3 hours. The precipitated crystals were collected by filtration and washed with dichloromethane to give 5.7 g of the objective compound. Purity (determined by iodometry), 87.5 %.

EXAMPLE 9

Preparation of D-α-(4-hydroxy-1,5-naphthyridine-3-carboxamido)-m-aminobenzylpenicillin triethylamine salt:-

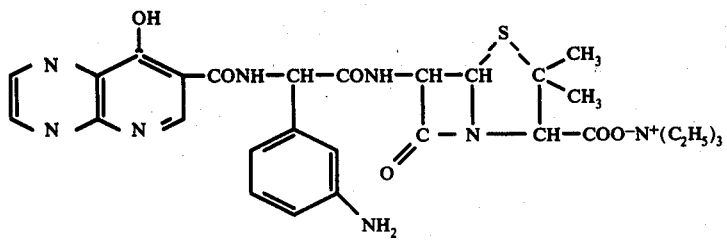

Ten grams of 5 % palladium-calcium carbonate were added to a solution of 2 g of D-α-(4-hydroxy-1,5-naphthyridine-3-carboxamido)-m-nitrobenzylpenicillin triethylamine salt in 50 ml of water, and the solution was shaken under a hydrogen atmosphere. Immediately after the absorption of hydrogen was completed, insoluble materials were removed by filtration, and the solution was freeze-dried to give the objective compound. Purity (determined by iodometry), 82 %.

EXAMPLES 10 – 41

In the same procedure as above, there were produced the penicillins (I) as shown in Table 1.

Table 1

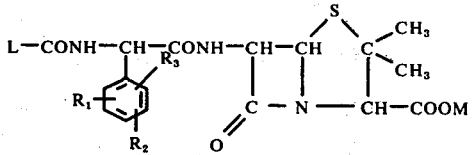

| Example No. | L | R₁ | R₂ | R₃ | M | Purity (%) |
|---|---|---|---|---|---|---|
| 10 | 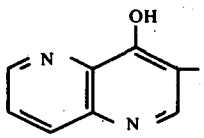 | p-NHC₂H₅ | H | H | Na | 87.3 |
| 11 | 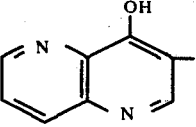 | m-I | H | H | Na | 88.2 |
| 12 | 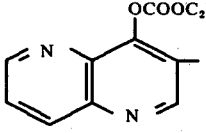 | m-Cl | H | H | H | 85 |
| 13 | 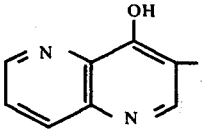 | p-CH₃ | H | H | Na | 89 |
| 14 | 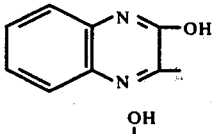 | m-NH₂ | H | H | Na | 90 |
| 15 | 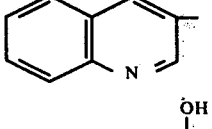 | m-NH₂ | H | H | Na | 88.5 |
| 16 | 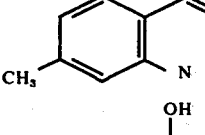 | m-NH₂ | H | H | Na | 83.5 |
| 17 | 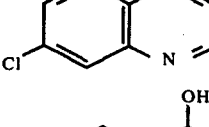 | p-NH₂ | H | H | Na | 90.1 |
| 18 | 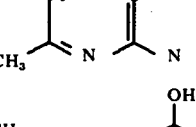 | m-NH₂ | H | H | Na | 90.5 |
| 19 | 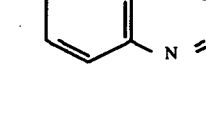 | m-NH₂ | H | H | Na | 89.3 |

Table 1-continued

Structure:
L—CONH—CH(R₃)—CONH—CH—CH—S—C(CH₃)₂
with phenyl bearing R₁, R₂; β-lactam ring C(=O)—N—CH—COOM

| Example No. | L | R₁ | R₂ | R₃ | M | Purity (%) |
|---|---|---|---|---|---|---|
| 20 | 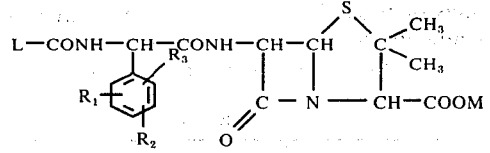 7-methoxy-4-hydroxyquinoline | m-NH₂ | H | H | Na | 87.2 |
| 21 | 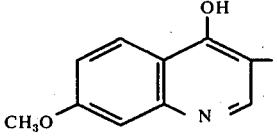 2-methyl-4-hydroxy-1,5-naphthyridine | p-NH₂ | H | H | Na | 88.4 |
| 22 | 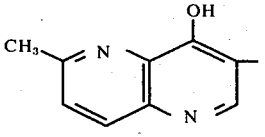 2-dimethylamino-4-hydroxy-1,5-naphthyridine | m-NH₂ | H | H | H | 92.7 |
| 23 | 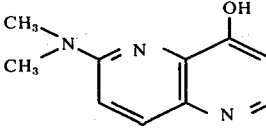 2-methoxy-4-hydroxy-1,5-naphthyridine | m-NH₂ | H | H | Na | 87.4 |
| 24 | 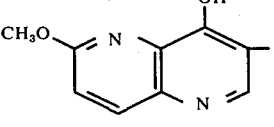 2-methylthio-4-hydroxy-1,5-naphthyridine | p-NH₂ | H | H | Na | 89.0 |
| 25 | 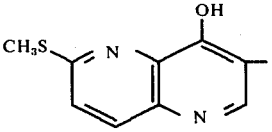 7-nitro-4-hydroxyquinoline | m-NH₂ | H | H | H | 82 |
| 26 | 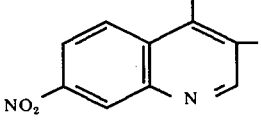 2-acetamido-4-hydroxy-1,5-naphthyridine | m-NH₂ | H | H | Na | 88.3 |
| 27 | 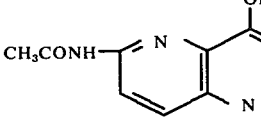 7-amino-4-hydroxyquinoline | m-NH₂ | H | H | H | 78.3 |
| 28 | 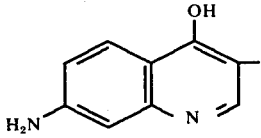 2-(benzyloxycarbonylamino)-4-hydroxy-1,5-naphthyridine | m-NH₂ | H | H | N(C₂H₅)₃ | 92.1 |
| 29 | 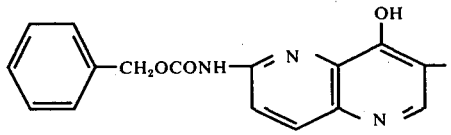 2-amino-4-hydroxy-1,5-naphthyridine | m-NH₂ | H | H | H | 83 |
| 30 | 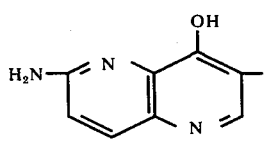 2-hydroxy-4-hydroxy-1,5-naphthyridine | m-NH₂ | H | H | Na | 87.5 |

Table 1-continued

| Example No. | L | $R_1$ | $R_2$ | $R_3$ | M | Purity (%) |
|---|---|---|---|---|---|---|
| 31 | quinolin-2-ol | m-NH$_2$ | H | H | Na | 88 |
| 32 | 2,4-dimethoxy-pyrido-pyrimidin-8-ol | p-NH$_2$ | H | H | Na | 88.4 |
| 33 | pyrido-pyrimidin-8-ol | m-NH$_2$ | H | H | Na | 85 |
| 34 | pyrazolo-pyridin-ol | p-OCH$_3$ | H | H | H | 79 |
| 35 | 2,4-dimethyl-pyrido-pyrimidin-8-ol | m-NH$_2$ | H | H | Na | 88 |
| 36 | methylenedioxy-quinolin-thiol | m-NH$_2$ | H | H | Na | 85 |
| 37 | naphthyridin-4-thiol | m-NH$_2$ | H | H | Na | 90.3 |
| 38 | quinolin-4-thiol | p-OCH$_3$ | H | H | Na | 89 |
| 39 | methoxy-pyrazino-pyridin-ol | m-NH$_2$ | H | H | Na | 88.9 |
| 40 | thiazolo-pyridin-ol | m-NH$_2$ | H | H | Na | 86.5 |

Table 1-continued
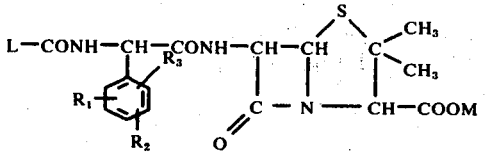
| Example No. | L | $R_1$ | $R_2$ | $R_3$ | M | Purity (%) |
|---|---|---|---|---|---|---|
| 41 | 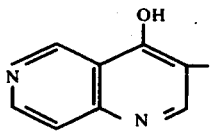 | p-OCH$_3$ | H | H | Na | 87.3 |
| 42 | 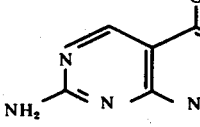 | m-NH$_2$ | H | H | N(C$_2$H$_5$)$_3$ | 83 |
| 43 | 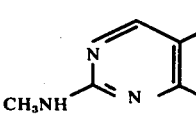 | m-NH$_2$ | H | H | Na | 87 |
| 44 | 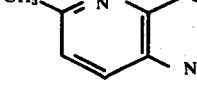 | p-OCH$_3$ | H | H | Na | 89.6 |
| 45 | 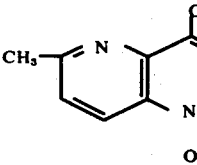 | p-N(CH$_3$)$_2$ | H | H | Na | 88 |
| 46 | 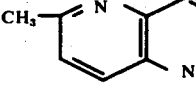 | p-OCH$_3$ | H | H | Na | 85.5 |
| 47 | 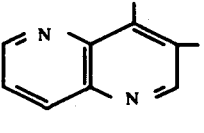 | m-F | H | H | Na | 88.5 |
| 48 | 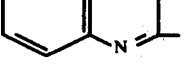 | m-F | H | H | Na | 87.3 |
| 49 | 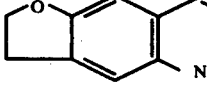 | m-NH$_2$ | H | H | Na | 85.7 |
| 50 | 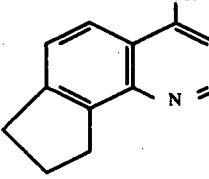 | m-NH$_2$ | H | H | Na | 80.5 |

Table 1-continued
| Example No. | L | R₁ | R₂ | R₃ | M | Purity (%) |
|---|---|---|---|---|---|---|
| 51 | 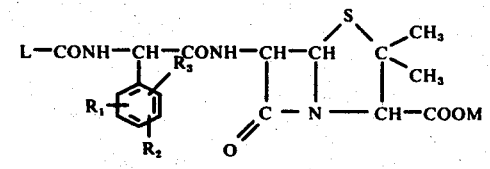 | m-NH₂ | H | H | Na | 89 |
| 52 | 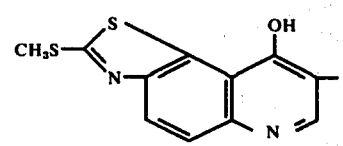 | p-NH₂ | H | H | Na | 83 |
| 53 | 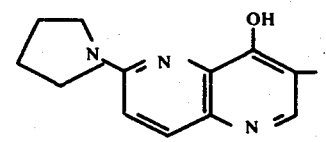 | m-NH₂ | H | H | Na | 87.8 |
| 54 | 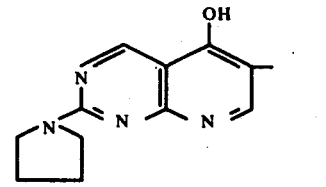 | p-NH₂ | H | H | Na | 85.1 |
| 55 | 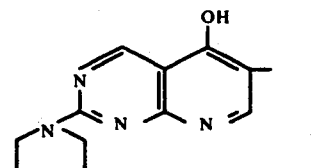 | m-NH₂ | H | H | Na | 80.5 |
| 56 | 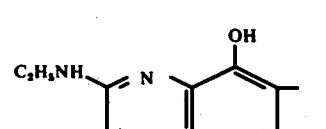 | m-NH₂ | H | H | Na | 75 |
| 57 | 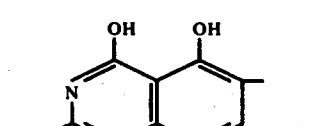 | m-NH₂ | H | H | Na | 83 |
| 58 | 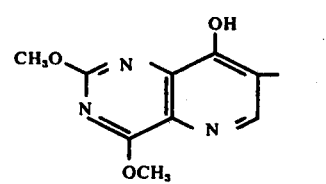 | m-NH₂ | H | H | Na | 87 |

Table 1-continued

L—CONH—CH—CONH—CH—CH(S)—C(CH₃)(CH₃)... C(=O)—N—CH—COOM (penicillin structure with R₁, R₂, R₃ substituents on phenyl)

| Example No. | L | R₁ | R₂ | R₃ | M | Purity (%) |
|---|---|---|---|---|---|---|
| 59 | 4-OH-1-ethyl-pyrazolo[3,4-b]pyridine | p-NH₂ | H | H | K | 88.1 |
| 60 | 4-OH-1,5-naphthyridine | p-OH | m-CH₃ | H | Na | 83 |
| 61 | 4-OH-1,5-naphthyridine | p-OH | m-OH | H | Na | 85 |
| 62 | 4-OH-1,5-naphthyridine | p-OH | m-NO₂ | H | Na | 78 |
| 63 | 4-OH-1,5-naphthyridine | p-OH | m-NH₂ | H | N(C₂H₅)₃ | 75 |
| 64 | 4-OH-1,5-naphthyridine | p-OH | m-OCH₃ | H | Na | 81 |

When determined according to the agar dilution method, the penicillins (I) afford the minimal inhibitory concentrations against test microorganisms as shown in Table 2.

Table 2

| | Minimal inhibitory concentration (μg/ml) | | | | | |
|---|---|---|---|---|---|---|
| Example No. | Staphylococcus aureus 209P | Escherichia coli NIHJ | Proteus miravilis GN2425 | Proteus vulgaris HV19 | Klebsiella pneumoniae PCI602 | Pseudomonas aeruginosa 104 |
| 1 | 1.56 | 0.78 | 0.78 | 0.025 | 6.25 | 1.56 |
| 2 | 1.56 | 0.78 | 1.56 | 0.025 | 12.5 | 1.56 |
| 3 | 1.56 | 3.13 | 6.25 | 0.1 | 12.5 | 3.13 |
| 4 | 1.56 | 3.13 | 12.5 | 0.1 | 12.5 | 3.13 |
| 5 | 1.56 | 3.13 | 6.25 | 0.1 | 6.25 | 1.56 |
| 6 | 1.56 | 6.25 | 12.5 | 0.78 | 12.5 | 6.25 |
| 7 | 0.78 | 3.13 | 6.25 | 0.2 | 6.25 | 6.25 |
| 10 | 1.56 | 0.78 | 0.78 | 0.05 | 12.5 | 1.56 |
| 11 | 1.56 | 1.56 | 1.56 | 0.05 | 12.5 | 3.13 |
| 12 | 1.56 | 1.56 | 1.56 | 0.05 | 12.5 | 3.13 |
| 13 | 1.56 | 0.78 | 1.56 | 0.05 | 6.25 | 1.56 |
| 14 | 0.78 | 3.13 | 12.5 | 0.78 | 12.5 | 0.78 |
| 15 | 0.78 | 3.13 | 3.13 | 0.2 | 6.25 | 3.13 |
| 16 | 0.78 | 6.25 | 3.13 | 0.39 | — | 3.13 |

Table 2-continued

| Example No. | Minimal inhibitory concentration (μg/ml) | | | | | |
|---|---|---|---|---|---|---|
| | Staphylo-coccus aureus 209P | Escheri-chia coli NIHJ | Proteus miravilis GN2425 | Proteus vulgaris HV19 | Klebsie-lla pneumo-niae PCI602 | Pseudo-monas aerugi-nosa 104 |
| 17 | 0.78 | 3.13 | 3.13 | 0.2 | 6.25 | 3.13 |
| 18 | 1.56 | 1.56 | 1.56 | 0.025 | 6.25 | 1.56 |
| 19 | 1.56 | 0.78 | 0.78 | 0.025 | 6.25 | 0.78 |
| 20 | 0.78 | 3.13 | 3.13 | 0.1 | 6.25 | 3.13 |
| 21 | 1.56 | 0.78 | 1.56 | 0.025 | 3.13 | 0.78 |
| 22 | 1.56 | 0.78 | 0.78 | 0.025 | 3.13 | 0.78 |
| 23 | 1.56 | 0.78 | 1.56 | 0.05 | 6.25 | 1.56 |
| 24 | 1.56 | 0.78 | 0.78 | 0.025 | 6.25 | 1.56 |
| 25 | 0.78 | 3.13 | 3.13 | 0.2 | 12.5 | 3.13 |
| 26 | 1.56 | 0.78 | 0.78 | 0.025 | 6.25 | 0.78 |
| 27 | 0.78 | 3.13 | 3.13 | 0.39 | 12.5 | 3.13 |
| 28 | 1.56 | 1.56 | 1.56 | 0.05 | 6.25 | 1.56 |
| 29 | 1.56 | 0.78 | 0.78 | 0.025 | 6.25 | 0.78 |
| 30 | 1.56 | 0.78 | 1.56 | 0.05 | 6.25 | 1.56 |
| 31 | 0.78 | 3.13 | 3.13 | 0.39 | 12.5 | 3.13 |
| 32 | 1.56 | 3.13 | 3.13 | 0.05 | 12.5 | 3.13 |
| 33 | 1.56 | 0.78 | 0.78 | 0.025 | 6.25 | 0.78 |
| 34 | 0.78 | 3.13 | 6.25 | 0.1 | 12.5 | 3.13 |
| 35 | 1.56 | 0.78 | 1.56 | 0.025 | 6.25 | 1.56 |
| 36 | 0.78 | 6.25 | 6.25 | 0.39 | 12.5 | 3.13 |
| 37 | 1.56 | 1.56 | 1.56 | 0.05 | 12.5 | 0.78 |
| 38 | 0.78 | 6.25 | 6.25 | 0.39 | 12.5 | 3.13 |
| 39 | 0.78 | 0.78 | 0.78 | 0.025 | 6.25 | 0.78 |
| 40 | 1.56 | 1.56 | 1.56 | 0.025 | 6.25 | 1.56 |
| 41 | 1.56 | 3.13 | 12.5 | 0.39 | 12.5 | 3.13 |
| 42 | 1.56 | 3.13 | 1.56 | 0.05 | 12.5 | 3.13 |
| 43 | 1.56 | 3.13 | 1.56 | 0.05 | 12.5 | 3.13 |
| 44 | 1.56 | 3.13 | 6.25 | 0.05 | 12.5 | 3.13 |
| 45 | 1.56 | 3.13 | 6.25 | 0.1 | 6.25 | 1.56 |
| 46 | 1.56 | 3.13 | 12.5 | 0.1 | 12.5 | 3.13 |
| 47 | 1.56 | 1.56 | 1.56 | 0.05 | 12.5 | 1.56 |
| 48 | 0.78 | 3.13 | 12.5 | 0.2 | 12.5 | 1.56 |
| 49 | 0.78 | 3.13 | 3.13 | 0.2 | 6.25 | 3.13 |
| 50 | 0.78 | 3.13 | 12.5 | 0.39 | 12.5 | 3.13 |
| 51 | 0.78 | 3.13 | 3.13 | 0.2 | 6.25 | 3.13 |
| 52 | 1.56 | 0.78 | 1.56 | 0.05 | 6.25 | 1.56 |
| 53 | 1.56 | 3.13 | 3.13 | 0.025 | 6.25 | 3.13 |
| 54 | 1.56 | 3.13 | 3.13 | 0.05 | 6.25 | 3.13 |
| 55 | 1.56 | 0.78 | 0.78 | 0.025 | 6.25 | 1.56 |
| 56 | 1.56 | 1.56 | 3.13 | 0.05 | 6.25 | 3.13 |
| 57 | 1.56 | 0.78 | 1.56 | 0.025 | 6.25 | 1.56 |
| 58 | 1.56 | 1.56 | 3.13 | 0.05 | 12.5 | 3.13 |
| 59 | 0.78 | 3.13 | 6.25 | 0.1 | 12.5 | 1.56 |
| 60 | 0.78 | 0.78 | 1.56 | 0.05 | 6.25 | 1.56 |
| 61 | 0.78 | 0.78 | 1.56 | 0.025 | 12.5 | 1.56 |
| 62 | 1.56 | 1.56 | 3.13 | 0.05 | 12.5 | 1.56 |
| 63 | 0.78 | 0.78 | 1.56 | 0.025 | 6.25 | 1.56 |
| 64 | 1.56 | 3.13 | 3.13 | 0.05 | 12.5 | 1.56 |
| Ampi-cillin | 0.1 | 6.26 | 1.56 | 1.56 | 50 | >500 |
| Amoxy-cillin | 0.2 | 12.5 | 3.13 | 12.5 | >200 | >200 |
| Car-beni-cillin | 0.78 | 12.5 | 0.78 | 0.78 | 200 | 50–100 |

What is claimed is:

1. A penicillin of the formula:

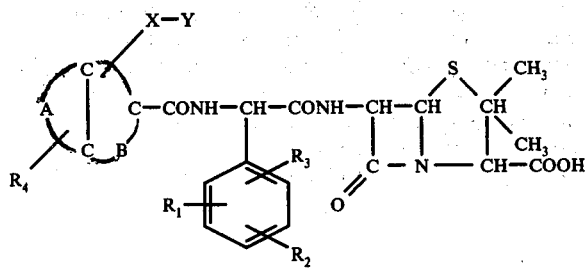

wherein

is a benzene ring or a pyridine ring, a pyrazine ring, a pyridazine ring, a pyrimidine ring, a pyrazole ring, a thiazole ring or an imidazole ring, $R_4$ is hydrogen, halogen, lower alkyl, lower alkoxy, lower alkylthio, hydroxyl, di(lower)alkylamino or lower alkanoylamino

is pyridine ring, a pyrazine ring or a pyridazine ring, X is oxygen or sulfur, Y is hydrogen, lower alkoxycarbonyl or lower alkanoyl and $R_1$, $R_2$ and $R_3$ are each hydrogen, halogen, nitro, lower alkylamino, di(lower-)alkylamino, amino, lower alkoxycarbonylamino, lower alkanoylamino, amino(lower)alkyl, lower alkyl, lower alkoxy, hydroxyl, sulfamoyl, trifluoromethyl, lower alkylthio or lower alkylsulfonyl, excluding the cases where all of $R_1$, $R_2$ and $R_3$ are hydrogen and where $R_1$ is hydroxyl and $R_2$ and $R_3$ are each hydrogen or halogen, and non-toxic pharmaceutically acceptable salts thereof.

2. The penicillin of claim 1, wherein

is a pyridine ring.

3. The penicillin of claim 2, wherein

has no substituent thereon.

4. The penicillin of claim 1, wherein Y is hydrogen.

5. A penicillin of the formula:

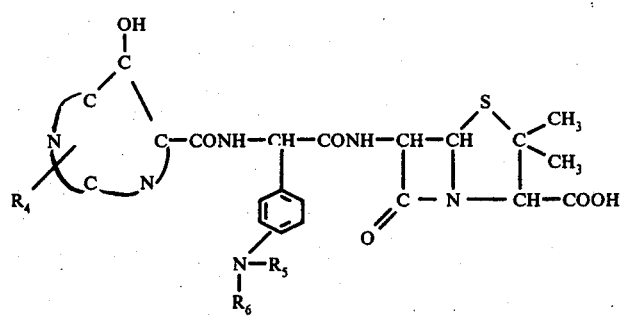

wherein

and

are each a pyridine ring, $R_4$ is hydrogen, halogen, lower alkyl, lower alkoxy, lower alkylthio, hydroxyl, di(-lower)alkylamino or lower alkanoylamino and $R_5$ and $R_6$ are each hydrogen, lower alkyl or lower alkanoyl, and non-toxic pharmaceutically acceptable salts thereof.

6. The penicillin of claim 5, wherein $R_4$ is hydrogen, methyl, methoxy or acetoamido,

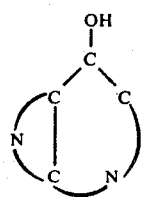

is 4-hydroxy-1,5-naphthyridine, $R_5$ is hydrogen and $R_6$ is hydrogen or acetyl.

7. A penicillin of the formula:

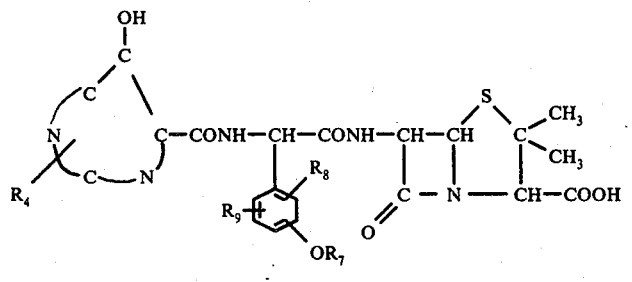

wherein

and

are each a pyridine ring, $R_4$ is hydrogen, halogen, lower alkyl, lower alkoxy, lower alkylthio, hydroxyl, di(-lower)alkylamino or lower alkanoylamino, $R_7$ is hydrogen or lower alkyl, $R_8$ is lower alkyl, amino, lower alkanoylamino, hydroxyl or lower alkoxy, and $R_9$ is hydrogen, lower alkyl, lower alkoxy or hydroxyl.

8. The penicillin of claim 7, wherein

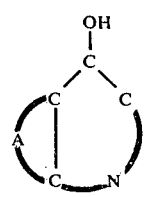

is 4-hydroxy-1,5-naphthyridine, $R_4$ is hydrogen, methyl, methoxy or acetamido, $R_7$ is hydrogen or methyl, $R_8$ is methyl, methoxy, amino, acetamido or hydroxyl and $R_9$ is hydrogen, methyl, methoxy or hydroxyl.

9. D-α-(4-Hydroxy-1,5-naphthyridine-3-carboxamido)-m-aminobenzylpenicillin and non-toxic pharmaceutically acceptable salts thereof.

10. D-α-(4-Hydroxy-1,5-naphthyridine-3-carboxamido)-p-aminobenzylpenicillin and non-toxic pharmaceutically acceptable salts thereof.

11. D-α-(4-Hydroxy-1,5-naphthyridine-3-carboxamido)-p-methoxybenzylpenicillin and non-toxic pharmaceutically acceptable salts thereof.

12. D-α-(4-Hydroxycinnolin-3-carboxamido)-m-aminobenzylpenicillin and non-toxic pharmaceutically acceptable salts thereof.

13. D-α-(3-Hydroxyquinoxaline-2-carboxamido)-m-aminobenzylpenicillin and non-toxic pharmaceutically acceptable salts thereof.

14. D-α-(4-Hydroxyquinoline-3-carboxamido)-m-aminobenzylpenicillin and non-toxic pharmaceutically acceptable salts thereof.

15. D-α-(4-Hydroxy-8-methyl-1,8-naphthyridine-3-carboxamido)-m-aminobenzylpenicillin and non-toxic pharmaceutically acceptable salts thereof.

16. D-α-(4-Hydroxy-6-methyl-1,5-naphthyridine-3-carboxamido)-m-aminobenzylpenicillin and non-toxic pharmaceutically acceptable salts thereof.

17. D-α-(4-Hydroxy-6-dimethylamino-1,5-naphthyridine-3-carboxamido)-m-aminobenzylpenicillin and non-toxic pharmaceutically acceptable salts thereof.

18. D-α-(4-Hydroxy-6-acetamido-1,5-naphthyridine-3-carboxamido)-m-aminobenzylpenicillin and non-toxic pharmaceutically acceptable salts thereof.

19. D-α-(8-Hydroxypyrido[3,2-d]pyridine-7-carboxamido)-m-aminobenzylpenicillin and non-toxic pharmaceutically acceptable salts thereof.

20. D-α-(4-Mercapto-1,5-naphthyridine-3-carboxamido)-m-aminobenzylpenicillin and non-toxic pharmaceutically acceptable salts thereof.

21. D-α-(8-Hydroxy-3-methoxypyrido[2,3-b]pyrazine-7-carboxamido)-m-aminobenzylpenicillin and non-toxic pharmaceutically acceptable salts thereof.

22. D-α-(4-Hydroxythiazolo[5,4-b]pyridine-5-carboxamido)-m-aminobenzylpenicillin and non-toxic pharmaceutically acceptable salts thereof.

23. D-α-(4-Hydroxy-1,5-naphthyridine-3-carboxamido)-p-hydroxy-m-methylbenzylpenicillin and non-toxic pharmaceutically acceptable salts thereof.

24. D-α-(4-Hydroxy-1,5-naphthyridine-3-carboxamido)-p,m-dihydroxybenzylpenicillin and non-toxic pharmaceutically acceptable salts thereof.

25. D-α-(4-Hydroxy-1,5-naphthyridine-3-carboxamido)-p-hydroxy-m-methoxybenzylpenicillin and non-toxic pharmaceutically acceptable salts thereof.

* * * * *